United States Patent
Lange

(10) Patent No.: US 8,912,495 B2
(45) Date of Patent: Dec. 16, 2014

(54) MULTI-SPECTRAL DEFECT INSPECTION FOR 3D WAFERS

(71) Applicant: KLA-Tencor Corporation, Milpitas, CA (US)

(72) Inventor: Steven R. Lange, Alamo, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 13/742,315

(22) Filed: Jan. 15, 2013

(65) Prior Publication Data

US 2014/0139822 A1    May 22, 2014

Related U.S. Application Data

(60) Provisional application No. 61/729,330, filed on Nov. 21, 2012.

(51) Int. Cl.
*G01J 5/00* (2006.01)
*G01N 21/95* (2006.01)
*G01N 21/35* (2014.01)

(52) U.S. Cl.
CPC ........ *G01N 21/3563* (2013.01); *G01N 21/9503* (2013.01); *G01N 21/359* (2013.01)
USPC ..................... 250/338.1; 250/559.4

(58) Field of Classification Search
CPC .................................................. G01N 21/86
USPC .......................................... 250/338.1, 559.4
See application file for complete search history.

(56) References Cited

U.S. PATENT DOCUMENTS

| | | | |
|---|---|---|---|
| 5,072,128 A | | 12/1991 | Hayano et al. |
| 5,264,912 A | * | 11/1993 | Vaught et al. ............... 356/237.5 |
| 5,386,119 A | * | 1/1995 | Ledger ........................ 250/341.8 |
| 5,608,526 A | | 3/1997 | Piwonka-Corle et al. |
| 5,684,565 A | * | 11/1997 | Oshida et al. ................... 355/53 |
| 5,859,424 A | | 1/1999 | Norton et al. |
| 6,483,580 B1 | | 11/2002 | Xu et al. |

(Continued)

FOREIGN PATENT DOCUMENTS

| | | |
|---|---|---|
| EP | 1 333 328 | 8/2003 |
| WO | 2012/082501 | 6/2012 |

OTHER PUBLICATIONS

Arceo et al., "Semiconductor metrology beyond 22nm: 3D memory metrology," Solid State Technology (online edition), Feb. 16, 2012.

(Continued)

*Primary Examiner* — David Porta
*Assistant Examiner* — Abra Fein
(74) *Attorney, Agent, or Firm* — Ann Marie Mewherter

(57) ABSTRACT

Multi-spectral defect inspection for 3D wafers is provided. One system configured to detect defects in one or more structures formed on a wafer includes an illumination subsystem configured to direct light in discrete spectral bands to the one or more structures formed on the wafer. At least some of the discrete spectral bands are in the near infrared (NIR) wavelength range. Each of the discrete spectral bands has a bandpass that is less than 100 nm. The system also includes a detection subsystem configured to generate output responsive to light in the discrete spectral bands reflected from the one or more structures. In addition, the system includes a computer subsystem configured to detect defects in the one or more structures on the wafer using the output.

22 Claims, 11 Drawing Sheets

(56) References Cited

U.S. PATENT DOCUMENTS

| | | | |
|---|---|---|---|
| 6,788,404 B2 | 9/2004 | Lange | |
| 6,891,627 B1 | 5/2005 | Levy et al. | |
| 6,900,892 B2 | 5/2005 | Shchegrov et al. | |
| 7,126,699 B1 | 10/2006 | Wihl et al. | |
| 7,358,494 B1* | 4/2008 | Gao et al. | 250/310 |
| 7,478,019 B2 | 1/2009 | Zangooie et al. | |
| 8,073,240 B2 | 12/2011 | Fischer et al. | |
| 8,237,213 B2 | 8/2012 | Liu | |
| 2002/0001364 A1* | 1/2002 | Opsal et al. | 378/88 |
| 2002/0006044 A1* | 1/2002 | Harbers et al. | 362/555 |
| 2002/0060791 A1 | 5/2002 | Stumbo et al. | |
| 2002/0109110 A1* | 8/2002 | Some et al. | 250/559.4 |
| 2003/0020009 A1* | 1/2003 | Sugiyama et al. | 250/234 |
| 2004/0179738 A1* | 9/2004 | Dai et al. | 382/218 |
| 2004/0207836 A1 | 10/2004 | Chhibber et al. | |
| 2004/0222358 A1* | 11/2004 | Bui et al. | 250/214.1 |
| 2004/0235205 A1 | 11/2004 | Levy et al. | |
| 2005/0133693 A1* | 6/2005 | Fouquet et al. | 250/214 R |
| 2005/0269522 A1* | 12/2005 | Farmer et al. | 250/458.1 |
| 2006/0164649 A1 | 7/2006 | Rosengaus | |
| 2006/0281266 A1 | 12/2006 | Wells | |
| 2007/0012887 A1* | 1/2007 | Letz et al. | 250/486.1 |
| 2007/0020784 A1 | 1/2007 | Timans et al. | |
| 2007/0195332 A1 | 8/2007 | Hwang et al. | |
| 2008/0277749 A1* | 11/2008 | Enichlmair et al. | 257/432 |
| 2009/0014624 A1* | 1/2009 | Blees et al. | 250/201.4 |
| 2010/0008588 A1* | 1/2010 | Feldkhun et al. | 382/206 |
| 2011/0170090 A1 | 7/2011 | Naftali et al. | |
| 2011/0278441 A1* | 11/2011 | Vermeulen et al. | 250/227.23 |
| 2011/0320149 A1 | 12/2011 | Lee et al. | |
| 2012/0171835 A1* | 7/2012 | Liu et al. | 438/381 |
| 2012/0257213 A1 | 10/2012 | Schonleber | |
| 2013/0116978 A1 | 5/2013 | Yoo et al. | |

OTHER PUBLICATIONS

Gostein et al., "Measuring deep-trench structures with model-based IR," Solid State Technology, vol. 49, No. 3, 38-42 (2006).

Jang et al., "Vertical Cell Array using TCAT (Terabit Cell Array Transistor) Technology for Ultra High Density NAND Flash Memory," 2009 Symposium on VLSI Technology Digest of Technical Papers, pp. 192-193, paper 10A-4, 2009.

Nahory et al., "Band gap versus composition and demonstration of Vegard's law for In1-xGaxAsyP1-y lattice matched to InP," Appl. Phys. Lett., 33(7), pp. 659-661, Oct. 1, 1978.

Scheel et al., "Electronic band structure of high-index silicon nanowires," phys. stat. sol. (b), pp. 1-6, Aug. 22, 2005.

International Search Report and Written Opinion for PCT/US2013/071111 mailed Mar. 12, 2014.

\* cited by examiner

MULTI-SPECTRAL DEFECT INSPECTION FOR 3D WAFERS

BACKGROUND OF THE INVENTION

1. Field of the Invention

The present invention generally relates to multi-spectral defect inspection for 3D wafers.

2. Description of the Related Art

The following description and examples are not admitted to be prior art by virtue of their inclusion in this section.

Semiconductor memory manufacturers, particularly Flash memory now and DRAM in the near future, have had trouble extending their shrinking design rule roadmap to smaller dimensions due to rapidly increasing costs for lithography and multiple process steps associated with pitch splitting techniques. The concept of going vertical has taken off with 3D or VNAND memory leading the way by building transistors (bits) vertically rather than orienting them in a planar manner which historically has been the rule. Early VNAND devices have 16 to 24 vertical bits with roadmaps quickly extending to 48 and 64 bits vertically and beyond. The changes are achieved with fewer process steps, relaxed lithography sizes, and lower manufacturing costs compared with the planar approach; hence, they're being quickly adopted.

The deposition of these thick stacks typically occurs in a single process step with subsequent processing on the whole stack to create the vertical transistors and connections. Wafer inspection for defects needs then to inspect the whole stack. For wafer inspection, these changes result in much thicker stacks of materials and structures, with the early VNAND devices having 2 um to 3 um thick stacks and eventual stacks in the 6 um to 8 um range (typical planar thicknesses are about 0.1 um to 1 um depending upon the process step). Defects in the processing steps can occur throughout these stacks and need to be detected and their source identified and corrected to ensure high manufacturing yields.

Accordingly, it would be advantageous to develop methods and systems for detecting defects in one or more structures on a wafer that have characteristics described above.

SUMMARY OF THE INVENTION

The following description of various embodiments is not to be construed in any way as limiting the subject matter of the appended claims.

One embodiment relates to a system configured to detect defects in one or more structures formed on a wafer. The system includes an illumination subsystem configured to direct light in discrete spectral bands to the one or more structures formed on the wafer. At least some of the discrete spectral bands are in the near infrared (NIR) wavelength range. Each of the discrete spectral bands has a bandpass that is less than 100 nm. The system also includes a detection subsystem configured to generate output responsive to light in the discrete spectral bands reflected from the one or more structures. In addition, the system includes a computer subsystem configured to detect defects in the one or more structures on the wafer using the output. The system may be further configured as described herein.

Another embodiment relates to a method for detecting defects in one or more structures formed on a wafer. The method includes directing light in discrete spectral bands to the one or more structures formed on the wafer. At least some of the discrete spectral bands are in the NIR wavelength range. Each of the discrete spectral bands has a bandpass that is less than 100 nm. The method also includes generating output responsive to light in the discrete spectral bands reflected from the one or more structures. In addition, the method includes detecting defects in the one or more structures on the wafer using the output.

Each of the steps of the method described above may be further performed as described herein. In addition, the method described above may include any other step(s) of any other method(s) described herein. Furthermore, the method described above may be performed by any of the systems described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
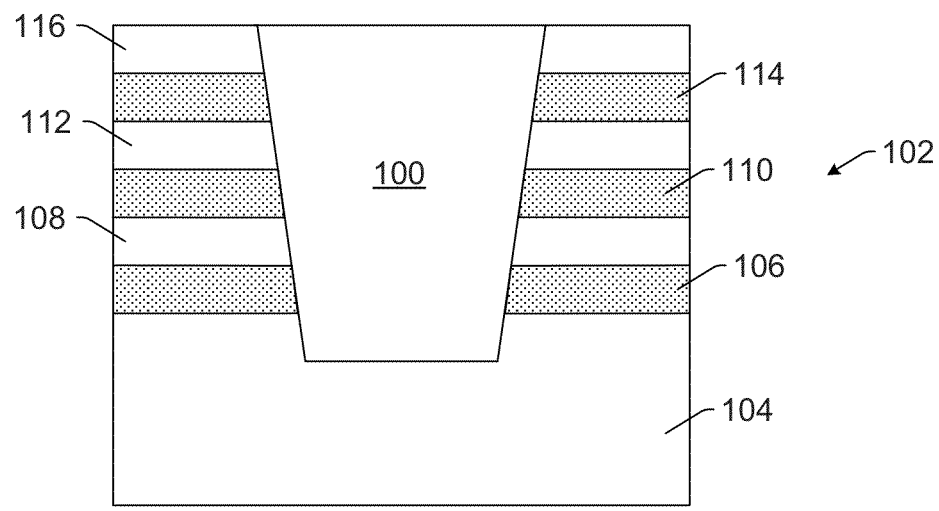
FIG. 1 is a schematic diagram illustrating a cross-sectional view of one embodiment of a structure in which defects may be detected by the embodiments described herein.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment relates to a system configured to detect defects in one or more structures formed on a wafer. In one embodiment, the one or more structures are formed through a stack of two or more layers, and the stack has a thickness greater than at least 1 um. For example, the one or more structures that can be inspected by the embodiments described herein include structures that are oriented and built vertically such as 3D or VNAND memory rather than being oriented and built in a planar manner. In one such example, as shown in FIG. 1, the one or more structures may include trench 100 formed through stack 102 of layers 106, 108, 110, 112, 114, and 116 and even into bottommost layer 104. As described further herein, layers 104, 106, 108, 110, 112, 114, and 116 may include alternating layers of materials that have different properties including different optical properties.

In one embodiment, the one or more structures are formed through a stack of two or more layers of material, and at least some of the two or more layers include polysilicon. For example, as shown in FIG. 1, the stack may include layers 106, 108, 110, 112, 114, and 116, and layers 106, 110, and 114 may be polysilicon while layers 104, 108, 112, and 116 may be formed of oxide. Such a structure may be further configured as described herein.

VNAND stacks can be divided into two architectures, gate first and gate last. Gate first architecture has a stack of alternating layers of oxide and polysilicon (OPOP) to make up each bit, and the gate last has alternating layers of oxide and silicon nitride (ONON). The important part is that polysilicon is substantially opaque for wavelengths below 450 nm and gradually becomes more transparent at longer wavelengths and completely transparent at about 1.06 um. Wafer inspection systems will need to get light into the stack of polysilicon to the defect location and then back out to obtain a signal. This implies that longer wavelengths are needed for these wafer types.

In one embodiment, the one or more structures include one or more opaque metallic structures such as tungsten structures formed through a stack of two or more layers of material. In another embodiment, the one or more structures are formed through a stack of two or more layers of material, and at least some of the two or more layers comprise an opaque conductor such as tungsten. For example, for the ONON stack, all of the materials are transparent above about 240 nm; so, commonly available wafer inspection systems can see well into these stacks. However, later on in the fabrication process, the silicon nitride is replaced by tungsten, which is opaque to all wavelengths. The process where this replacement occurs involves etching a deep trench through all of the layers, using a wet etch chemistry to remove the silicon nitride, and then depositing the tungsten using the trench. In one such example, as shown in FIG. 1, layers 104, 108, 112, and 116 may be silicon oxide while layers 106, 110, and 114 may be silicon nitride. Therefore, layers 106, 110, and 114 may be replaced by tungsten using a process such as that described above, and tungsten may also be formed in trench 100, which has been formed through the stack, to form a tungsten plug.

It turns out that light at longer wavelengths (greater than 600 nm) can penetrate into the trench if the light is polarized in a direction perpendicular to the trench. So, again, longer wavelengths are advantageous for inspecting the ONON layers after the tungsten replacement. Thus, for many inspection layers on VNAND devices, longer wavelength light is needed for inspection, but currently available wafer inspection systems typically have wavelengths between 260 nm and 450 nm and thus are not well suited for inspecting these devices. In particular, currently available inspection systems that have wavelengths between 260 nm and 450 nm can only inspect a few of the layers for the VNAND devices. For example, simulations of the e-field penetration into a tungsten slot, that is 1 um thick, as a function of wavelength for polarization perpendicular to the trench showed that longer wavelengths (e.g., longer than 450 nm) penetrate to the bottom of the trench while shorter wavelengths cannot penetrate to the bottom of the trench and, in some cases, cannot penetrate at all. In addition, the e-field in a 1 um high tungsten trench was simulated with HEF polarization (horizontal electric field perpendicular to the trench), which showed good penetration at 633 nm, and with VEF (vertical electric field parallel to the trench), which showed zero penetration at the same wavelength.

Figure 7:
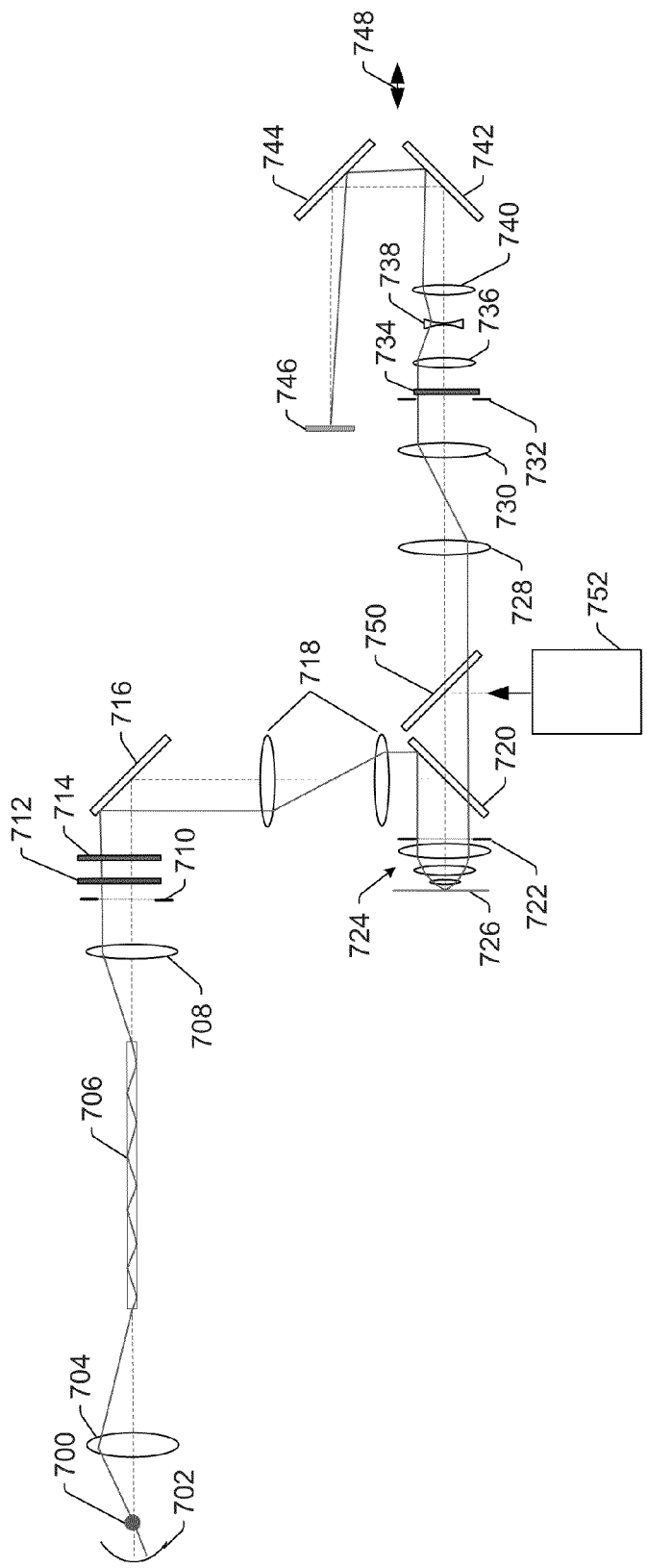
FIG. 7 is a schematic diagram illustrating a side view of one embodiment of a system configured to detect defects in one or more structures formed on a wafer.

Taking all of the above into consideration, the system embodiments described herein include an illumination subsystem configured to direct light in discrete spectral bands to the one or more structures formed on the wafer, at least some of the discrete spectral bands are in the near infrared (NIR) wavelength range, and each of the discrete spectral bands has a bandpass that is less than 100 nm. Such an illumination subsystem may be configured as shown in FIG. 7 described further herein, for example. In one embodiment, the discrete spectral bands are in a wavelength range from 500 nm to 950 nm. For example, the system may be implemented by altering a basic brightfield (BF) wafer inspection system to have longer wavelengths (e.g., about 500 nm or 600 nm to about 950 nm), optional polarization control for parallel and perpendicular c-field as described further herein, and a set of spectral subbands, which may in some embodiments be provided by a set of subband wavelength filters, across the entire operating wavelength range. As will be described further herein, the set of spectral subbands is used to provide information about the depths of defects, the types of defects, and to increase, and even maximize, the defect signal due to the defect signal variation with wavelength.

In one embodiment, each of the discrete spectral bands is separated by a wavelength of at least 1 nm. In other words, the discrete spectral bands of the light that are directed to the wafer are not continuous over an entire larger wavelength range that encompasses all or some of the discrete spectral bands. For example, the discrete spectral bands of the light are not directed to the wafer as broadband light. In other words, in the embodiments described herein, broadband light is not incident on the wafer (although as described further herein a broadband source can be used to provide at least some of the light in the discrete spectral bands). In still other words, although light such as broadband light that has some range of wavelengths may be considered to have a number of sub wavelength bands within that entire range, those subbands are not necessarily or inherently discrete unless the light from the source is acted upon by some other optical element(s) such as those described further herein.

Figure 2:
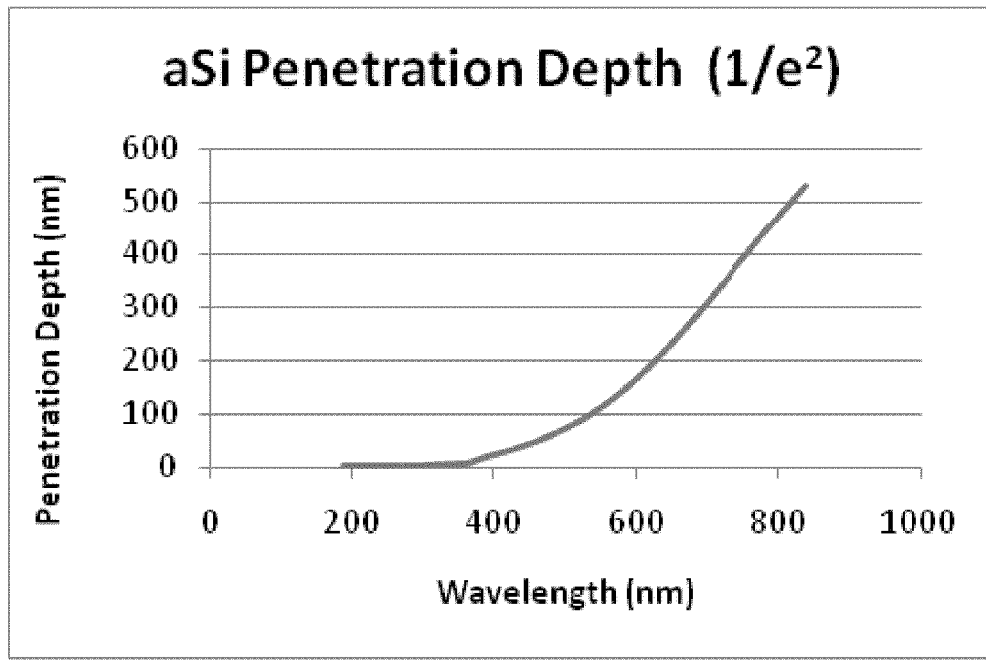
FIG. 2 is a plot illustrating the penetration depth of different wavelengths of light into amorphous silicon.
Figure 3:
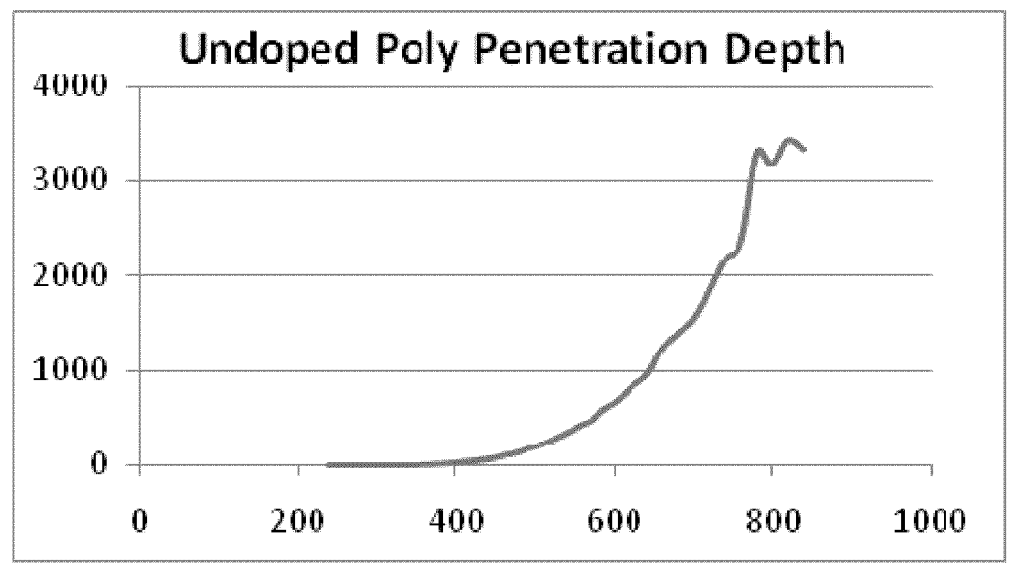
FIG. 3 is a plot illustrating the penetration depth of different wavelengths of light into undoped polysilicon.

In one embodiment, the light directed by the illumination subsystem to the one or more structures penetrates to different depths in the one or more structures depending on the discrete spectral bands of the light. For example, the penetration depth in polysilicon varies with wavelength with more penetration at longer wavelengths. FIG. 2 shows amorphous silicon (aSi) penetration depth as a function of wavelength. As shown in FIG. 2, if only a wavelength of 600 nm was chosen for a wafer inspection system, the light will penetrate only about 160 nm into the amorphous silicon. In addition, different wavelengths may be used to penetrate more or less into the material. Thus, if one performs multiple inspections at longer and longer wavelengths, the inspections will be sensitive to defects at deeper and deeper depths. So, looking at the signal as a function of wavelength is equivalent to looking at different depths in the wafer stack as a function of wavelength. FIG. 3 shows the penetration depth for undoped polysilicon, which shows similar depth versus wavelength characteristics as described above. Therefore, the embodiments described herein can use multiple wavebands to view different depths into OPOP stack wafers.

To understand how these material properties and wafer stacks with structures affect the inspection light, one can use various simulation codes (such as Finite Difference Time Domain or Rigorous Coupled Wave Algorithm) which solve Maxwell's equations for the propagation of electric fields and apply them to the inspection wavelengths and stacks of wafer materials. The output from these simulators can show the electric field penetration into the layers and the expected signal a wafer inspection tool will have. Inspection tool recipe options like wavelength, polarization, and illumination and collection aperture can be simulated as well to predict the tool's performance.

Another feature of the relatively thick stacks of the structures described herein is the interference causes standing e-field waves that show up as oscillating bands vertically in the trench. The spatial frequency of the bands is a function of wavelength with shorter wavelengths having more bands. What this means for wafer inspection is that the defect signal will oscillate as the defect varies its depth in the trench. So, if a single wavelength was used, the defect signal can change its sign relative to the background and can disappear at a null. To avoid this lack in sensitivity, one can scan the wafer with different wavelengths so that a null is not encountered between the wavelengths.

Figure 4:
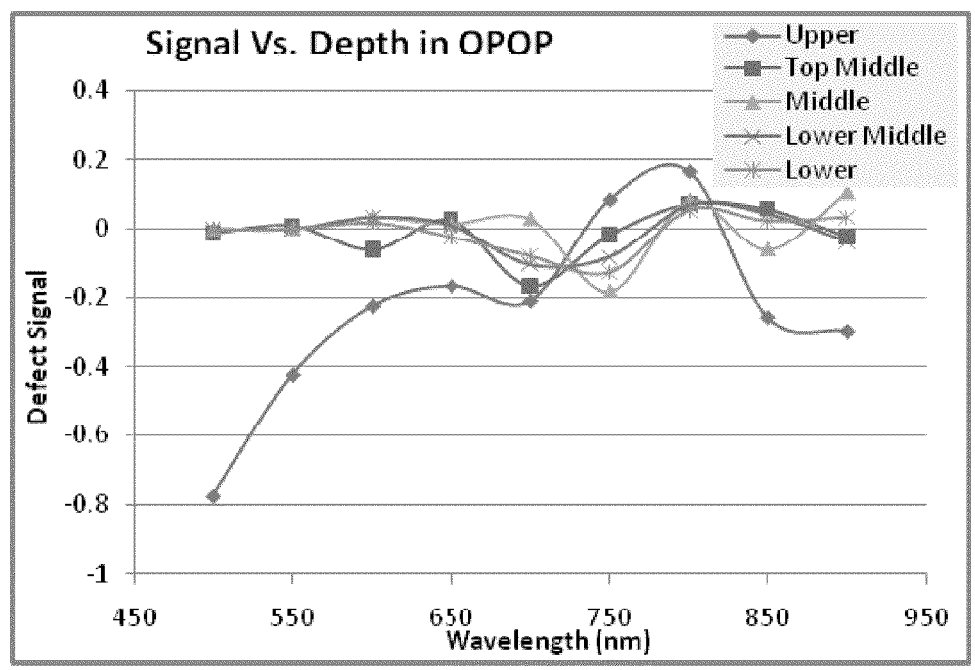
FIG. 4 is a plot illustrating simulated defect signals for an oxide-polysilicon-oxide-polysilicon (OPOP) deposition with a particle at various depths.

The signal as a function of depth was simulated with results shown in FIG. 4 for an OPOP deposition with a particle at various depths (upper, top middle, middle, lower middle, and lower) in the stack. These simulations were performed for a wafer inspection system aperture that causes illumination through only the outer part of the illumination pupil at longer wavelengths from 500 nm to 900 nm. (Light passing through such an aperture will appear, in cross-section, to have an annular shape, and thus such an aperture will be referred to herein as an "annular" aperture.) For the particle at the highest position in the OPOP stack (the "upper" particle), the signals at these wavelengths are generally strong with even the 500 nm wavelength having relatively good signal. As the depth of the particle increases (e.g., from upper to top middle and so forth), the signals at shorter wavelengths decrease but remain stronger at the longer wavelengths. The signal oscillation with wavelength that can be seen in this figure illustrates the changing of the standing-wave effect where wavelength changes the location of standing nodes causing the signal to vary. Similarly, wavelength can be used to discriminate depths in tungsten trenches with longer wavelengths seeing further into the trenches as described further herein.

Figure 5:
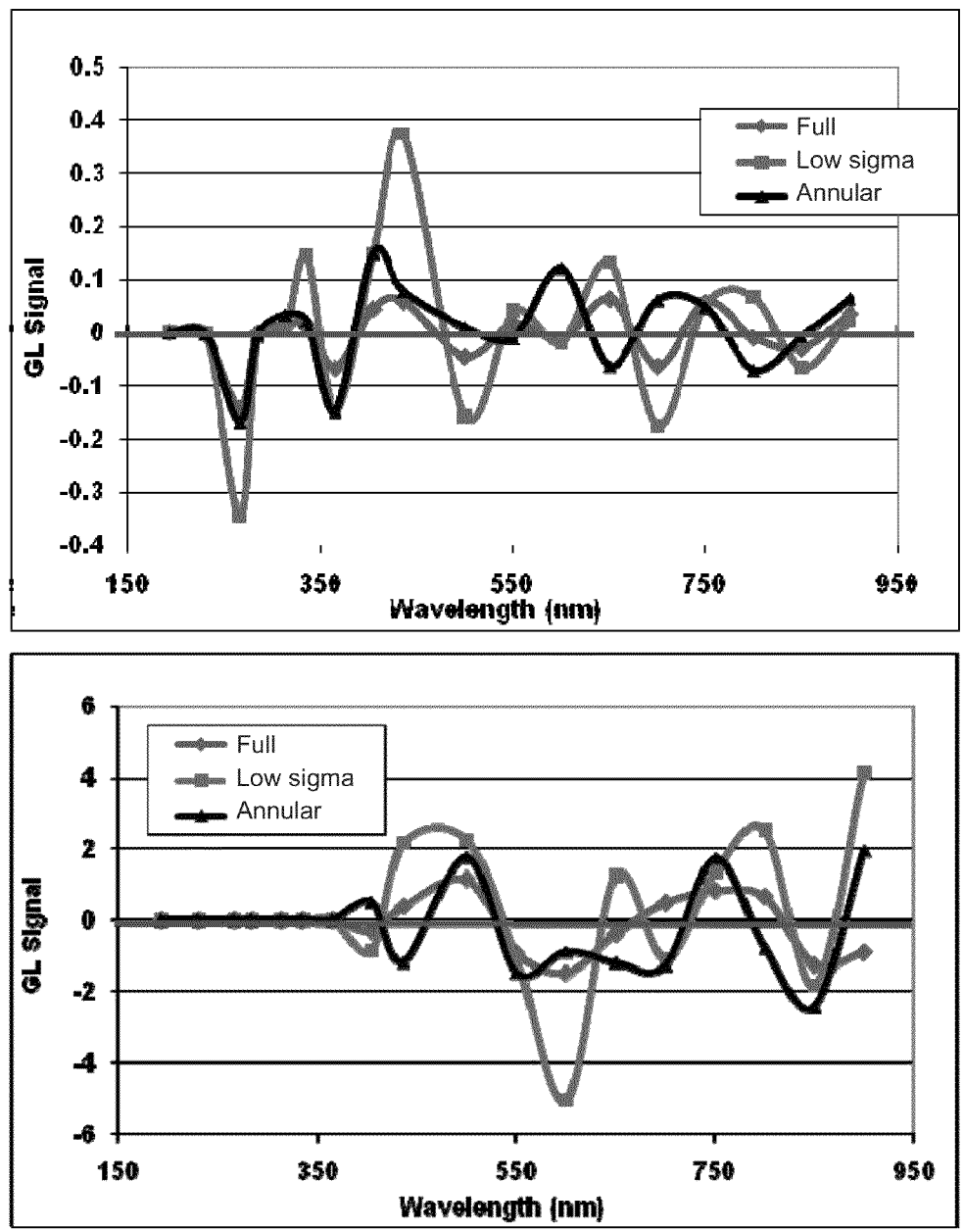
FIG. 5 includes plots illustrating simulated defect signals for different VNAND structures as a function of wavelength and aperture.

As noted above, each of the discrete spectral bands of light directed to the wafer by the illumination subsystem has a bandpass that is less than 100 nm. For example, scanning with a relatively small wavelength range has the advantage of collecting a relatively good signal, either positive or negative. If a broadband illumination source is used for the structures described herein, positive signals can cancel negative ones and leave the inspection system with substantially little overall signal. FIG. 5 shows simulations of defect signals in two different VNAND structures as a function of wavelength and different apertures (full (illumination across the entire available illumination pupil), low sigma (illumination through the center, but not the edge, of the illumination pupil), and annular (described further above)). As can be seen in FIG. 5, the defect signal changes phase from positive to negative with a wavelength period of about 100 nm. So, an inspection system with a waveband of 100 nm would average the positive and negative signals almost to zero, and an inspection system with a waveband greater than 100 nm will average more than 1 period resulting in a substantially low overall signal. The optimum waveband is possibly in the 50 nm range where one is likely to find either a maximum or minimum in the signal, albeit there will be cases where the signal can cancel out. It can be further minimized if repeat scans are performed with different apertures, like low-sigma and annular or full, which tend to be out of phase with each other.

One desirable output of inspection is the location of the defect in the stack and the type of defect since that information can aid in the correction or minimization of the defects to ensure higher yields. Therefore, one advantage of the embodiments described herein is that they can give information on the location of the defect in the stack and the type of defect. For example, the system includes a computer subsystem described further herein configured to detect defects in the one or more structures on the wafer using the output generated by a detection subsystem of the system, also described further herein. In one embodiment, the one or more structures are formed through a stack of two or more layers of material, and the computer subsystem is configured to determine a location of the defects within the stack.

Figure 6:
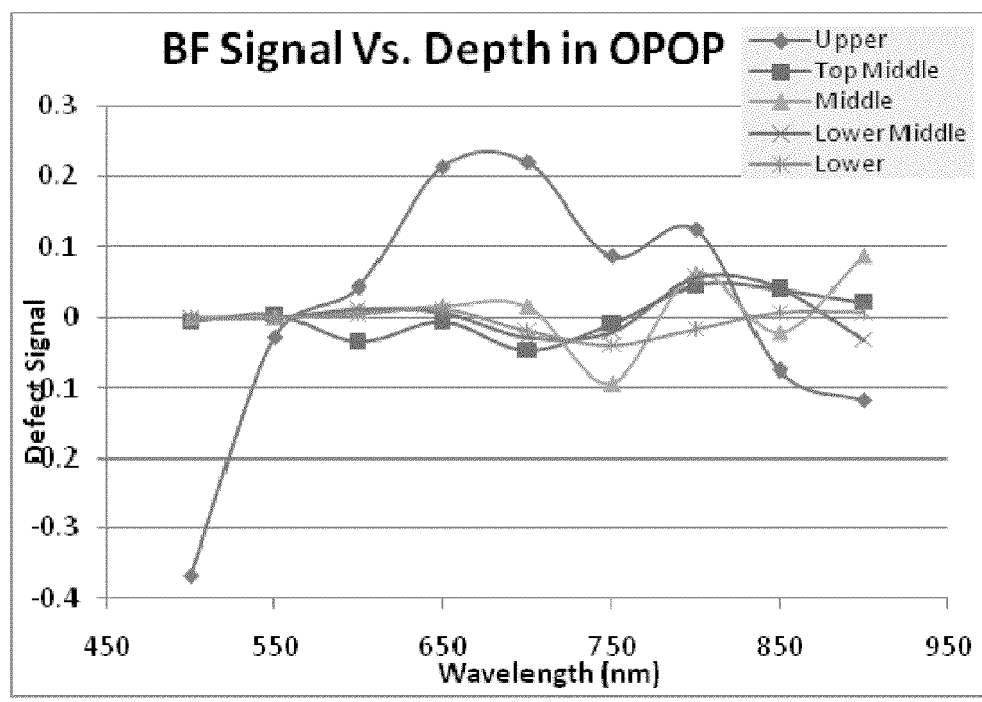
FIG. 6 is a plot illustrating simulated defect signals for an OPOP deposition with a particle at various depths.

To identify the depth of a defect fairly accurately, a test of the signal vs. wavelength can be performed for a given aperture and then this result can be compared with a set of simulations of the signal vs. various depths to match the observed signal to the simulated signal. While such a test may take too much time during an inspection, the test may be performed on selected defects (e.g., by running an Optics Selector session, which can be performed on tools commercially available from KLA-Tencor, Milpitas, Calif., and as described in U.S. Pat. No. 8,073,240 issued on Dec. 6, 2011 to Fischer et al. and U.S. Patent Application Publication No. 2011/0320149 published on Dec. 29, 2011 to Lee et al., which are incorporated by reference as if fully set forth herein) by varying the wavelength (e.g., using spectral filters such as those described further herein) and recording the signals of a defect paying attention to the sign of the signals. The BF simulations shown in FIG. 6 show that the signal changes fairly dramatically with wavelength when the defect is moved deeper into the structure (e.g., from the upper to the top middle to the middle to the lower middle and to the lower portions of the structure). To provide even more data to compare, apertures could also be incorporated in addition to the wavelength using the plot for the annular aperture described above. This technique is somewhat similar to the optical critical dimension (OCD) process of simulating thousands of structure variations and then matching observed BF reflection spectra to the simulated spectra and determining the CD from the closest matching spectra, which may be performed as described in U.S. Pat. No. 6,483,580 to Xu et al. issued Nov. 19, 2002 and U.S. Pat. No. 6,900,892 to Shchegrov et al. issued May 31, 2005, both of which are incorporated by reference as if fully set forth herein. In the embodiments described herein, however, a defect depth is matched to a simulated condition rather than the structure shape (e.g., CD). In a similar manner, a defect type may be determined by comparing the signal vs. wavelength and/or aperture to simulated signals. For example, in one embodiment, the one or more structures are formed through a stack of two or more layers of material, and the computer subsystem described herein is configured to determine a type of the defects.

FIG. 7 illustrates one embodiment of a system configured to detect defects in one or more structures formed on a wafer. As described further herein, the system includes an illumination subsystem configured to direct light in the discrete spectral bands described herein to the one or more structures formed on the wafer. In this embodiment, the illumination subsystem includes light source 700 configured to generate the light, mirror 702 configured to collect the light from the light source, and condenser lens 704 configured to focus the light from the light source and the mirror to the opening of light pipe 706, which scrambles the light to create a uniform distribution at the exit of the pipe. The illumination subsystem may also include collimating lens 708 configured to collect the light exiting the light pipe and to direct the light through pupil image plane 710, spectral filter 712, and optional polarizer 714 of the illumination subsystem. In addition, the illumination subsystem includes reflective optical element 716 configured to direct the light from the polarizer to pupil relay 718 of the illumination subsystem. The illumination subsystem further includes beam splitter 720 (e.g., a 50/50 beam splitter) configured to direct the light through system pupil 722 and objective lens 724 of the illumination subsystem to wafer 726.

Mirror 702, condenser lens 704, light pipe 706, collimating lens 708, reflective optical element 716, pupil relay 718, beam splitter 720, and objective lens 724 may include any suitable such elements known in the art. In addition, although some of the elements of the illumination subsystem are shown as single optical elements or formed of multiple optical elements, the number of optical elements included in any one element may vary depending on the configuration of the system. For example, the number of refractive optical elements included in objective lens 724 shown in FIG. 7 may vary from that shown. In addition, objective lens 724 and other optical elements of the illumination subsystem may be designed for NIR wavelengths with appropriate anti-reflective (AR) and high-reflective (HR) coatings for the optics in the path of the light.

In one embodiment, the illumination subsystem includes a broadband light source configured to generate at least two of the discrete spectral bands of light. For example, in one embodiment, light source 700 may be a Xenon broadband arc lamp or another similar lamp that can be used to provide the longer (e.g., NIR) wavelengths described herein. The broadband light source may generate light having wavelengths that span all of the discrete spectral bands of light, or multiple light sources may be used, each providing light having wavelengths that span only some of the discrete spectral bands of light.

In one such embodiment, the illumination subsystem includes two or more spectral filters configured to be positioned in a path of the light generated by the broadband light source, different spectral filters correspond to different discrete spectral bands, and the illumination subsystem is configured to sequentially position the spectral filters in the path such that the light in the discrete spectral bands is sequentially directed to the wafer. For example, spectral filter 712 shown in FIG. 7 may be one of several spectral filters that may be positioned in the path of the light generated by light source 700, which may be a broadband light source as described above. In one such example, the light source may be configured to provide light at wavelengths between 700 nm and 850 nm, and the center wavelength of each spectral filter may be spaced apart by 50 nm at 700 nm, 750 nm, 800 nm, and 850 nm with a 40 nm full width half maximum (FWHM) bandpass.

Figure 8:
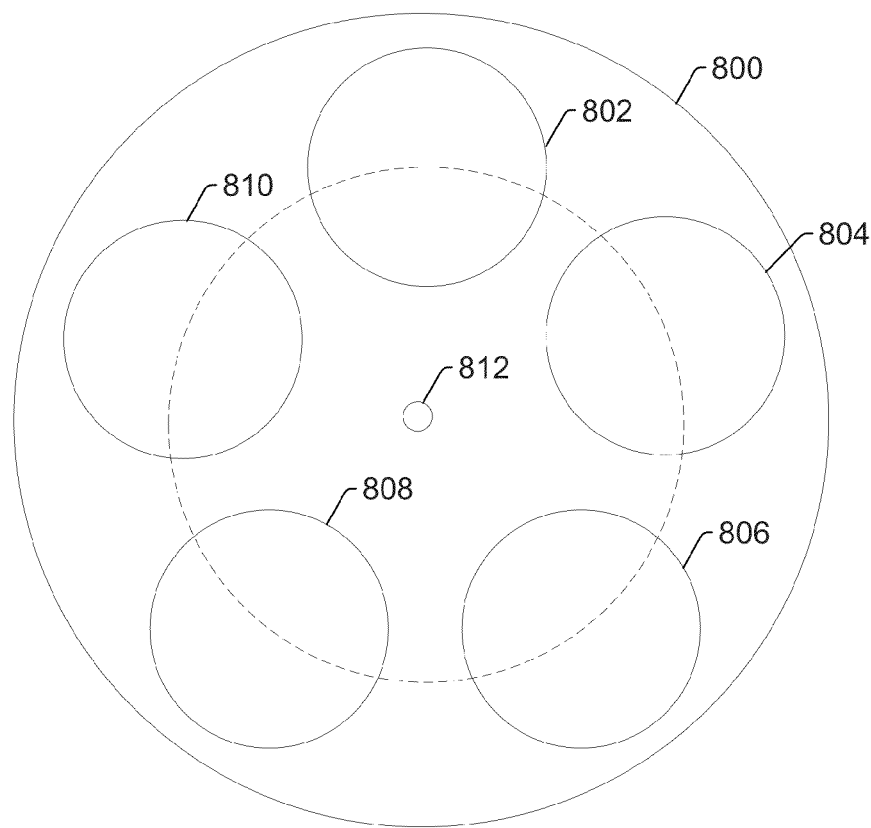
FIG. 8 is a schematic diagram illustrating a cross-sectional view of one embodiment of a spectral filter wheel that includes two or more spectral filters and that may be included in the system embodiments described herein.

In some such embodiments, the spectral filters may be arranged on a spectral filter wheel such as that shown in FIG. 8. For example, as shown in FIG. 8, spectral filter wheel 800 includes 5 different spectral filters (spectral filters 802, 804, 806, 808, and 810), and the spectral filter wheel may be coupled to axle 812 in any suitable manner such that the spectral filter wheel can be rotated by one or more elements (not shown) of the illumination subsystem (such as a mechanical, motorized, or robotic assembly). In this manner, the illumination subsystem may be configured to alter the spectral filter that is positioned in the path of the light from the light source. In addition, by rotating the spectral filter wheel, the illumination subsystem can sequentially move each of the spectral filters into the path of the light from the light source. Each of the spectral filters may be a bandpass filter whose wavelength range is matched to one of the discrete spectral bands. In this manner, light in the discrete spectral bands may be separately and sequentially directed to the wafer.

In one embodiment in which the one or more structures are formed through a stack of two or more layers of material, the illumination subsystem includes a polarizing component configured to alter a polarization of the light directed by the illumination subsystem to the one or more structures such that the polarization of the light is substantially perpendicular to the one or more structures. In another embodiment, the one or more structures include one or more trenches formed through a stack of two or more layers of material, and the illumination subsystem includes a polarizing component configured to alter a polarization of the light directed by the illumination subsystem to the one or more trenches such that the polarization of the light is substantially perpendicular to the one or more trenches. Such structures that include trenches may be further configured as described herein. For example, in one embodiment, at least one of the two or more layers of material in the stack includes tungsten. In both such embodiments, polarizer 714 shown in FIG. 7 may be used as such a polarizing component. Polarizer 714 may be optional, and the illumination subsystem may be configured to rotate the polarizer in any suitable manner for parallel and perpendicular orientations with respect to the wafer. In addition, as shown in FIG. 7, polarizer 714 may be located relatively near the spectral filter(s).

The system also includes a detection subsystem configured to generate output responsive to light in the discrete spectral bands reflected from the one or more structures. For example, as shown in FIG. 7, the detection subsystem includes objective lens 724 that is configured to collect the light reflected by the one or more structures. Therefore, the illumination and detection subsystems may share a common objective. The detection subsystem also includes beam splitter 720 that is configured to transmit the light collected by the objective lens. Beam splitter 720 may be further configured as described above. In addition, the detection subsystem includes a pupil relay magnification tube that is formed by refractive optical elements 728 and 730, which may include any suitable refractive or reflective optical elements known in the art. The detection subsystem may also include pupil image plane 732 and polarizer 734, which may include any suitable polarizing component. The detection subsystem further includes a zooming lens group made up of refractive optical elements 736, 738, and 740, which may include any suitable refractive or reflective optical elements known in the art. In addition, the detection subsystem may include trombone mirrors 742 and 744, which may include any suitable reflective optical elements. The detection subsystem further includes detector 746, which may include any suitable detector such as a charge coupled device (CCD). Other embodiments may not include the pupil relay or zoom and have a fixed magnification.

In this manner, light reflected by the one or more structures may be collected by objective lens 724, transmitted through beam splitter 720, collected from the beam splitter by the pupil relay magnification tube that directs the light through pupil image plane 732 and polarizer 734 to the zooming lens group. The zooming lens group directs the light to the trombone mirrors, which reflect and focus the light to the detector, which generates the output responsive to the light in the discrete spectral bands reflected from the one or more structures. The output may include any suitable output known in the art such as signals, image signals, data, image data, and the like. The detector shown in FIG. 7 may be capable of detecting light in all of the discrete spectral bands and producing output in response thereto. However, the detector may be replaced with multiple detectors (not shown), each used to detect light in only some of the discrete spectral bands.

The system may be designed with various magnifications to sample the BF or dark field (DF) image that is created by various apertures in the incident and reflected light paths. For example, as shown in FIG. 7, the pupil relay magnification tube, the zooming lens group, and the trombone mirrors may be used to alter the magnification of the detection subsystem depending on the aperture used for inspection and/or to optimize the performance of the system for any other factors. In addition, the system may be configured to move the trombone mirrors back and forth as shown by arrow 748 to compensate for changes in the magnification of the pupil relay magnification tube and/or the zooming lens group. Like the objective lens, the magnification tube should be designed for NIR wavelengths with appropriate AR and HR coatings for the optics in the path.

The illumination and detection subsystems may include additional optical elements such as apertures, which may be positioned, for example, at the position(s) of pupil image plane 710 and/or pupil image plane 732. In addition, the system may be configured such that different apertures can be used for the same structures or different apertures can be used for different structures. For example, the system may be configured to move apertures into and out of the path of light as described above with respect to the spectral filters and the aperture used is independent of the spectral filter used.

In one such embodiment, the illumination subsystem includes first and second apertures that are different from each other. The illumination subsystem is configured to scan the light in the discrete spectral bands across the wafer using the first aperture and then the second aperture, and the computer subsystem described further herein is configured to detect the defects in the one or more structures on the wafer using the output generated by scanning performed with the first and second apertures. In this manner, different scans of the wafer can be performed with different apertures. For example, one scan may be performed with a low sigma aperture, and a second scan may be performed with an annular or BF aperture. Such scans may be performed because they tend to be out of phase with each other and can therefore minimize the chance that the signals from any one defect within any one of the discrete spectral bands will cancel themselves out. In this manner, the output acquired by each scan may be a separate data set. The separate data sets may be used to try to determine what the defect was, based upon the results of the scans. In addition, repeating scans with different apertures (and/or different wavelengths as described further herein) may be performed to get a higher capture rate of the defects in the stack.

The system and each of the subsystems may include any other suitable optical elements. For example, the detection subsystem may include an IR filter (not shown). In addition, the detection subsystem may include a Y-mirror (not shown) that tilts the image of the wafer relative to the detector and is used to align a swath across dies during scanning so that the image of each part of the die lands on exactly the same pixel in the detector (which may be part of run time alignment (RTA)). The system may also include an auto-focus subsystem. For example, as shown in FIG. 7, the system may include beam splitter 750 positioned in the path of the light from the wafer. The beam splitter may be coupled to auto-focus subsystem 752, which may include any suitable combination of optical elements. Beam splitter 750 may direct light from the auto-focus subsystem to the wafer and direct that light reflected from the wafer back to the auto-focus subsystem such that it can be used to determine and correct the focus position of the system.

The system shown in FIG. 7 also includes a computer subsystem (such as computer system 1404 shown in FIG. 14) configured to detect defects in the one or more structures on the wafer using the output. For example, the computer subsystem may be coupled to the detector(s) of the detection subsystem by one or more transmission media, which may include "wired" and/or "wireless" transmission media, such that the computer subsystem can receive the output generated by the detector(s). The computer subsystem may be configured to use the output and any suitable algorithm and/or method to detect the defects.

Using spectral filter(s) with a broadband light source as described above may be advantageous since it has relatively low coherence and would typically have less wafer noise. However, other light sources can be used in the embodiments described herein. For example, in one embodiment, the illumination subsystem includes light emitting diodes (LEDs), each of the LEDs is configured to provide the light in only one of the discrete spectral bands, and each of the LEDs has a bandwidth that is spaced from bandwidths of other LEDs in the illumination subsystem by at least 20 nm. In this manner, the embodiments may use a set of LEDs across the NIR range spaced 20 nm to 70 nm apart. In other words, the center wavelength of one LED may be spaced by about 20 nm to 70 nm from the center wavelength of another LED. LEDs are relatively incoherent sources with bandwidths on the order of 10 nm and would not contribute to excessive wafer noise. LEDs are unpolarized light sources and like the arc lamp described above may be used with a separately polarizing filter (e.g., polarizer 714 shown in FIG. 7) that can be rotated.

In another embodiment, the illumination subsystem includes laser diodes, each of the laser diodes is configured to provide the light in only one of the discrete spectral bands, and each of the laser diodes has a bandwidth that is spaced from bandwidths of other laser diodes in the illumination subsystem by at least 20 nm. For example, the embodiments described herein may use a set of NIR laser diodes spaced out 20 nm to 70 nm apart. Light from the laser diodes may be speckle busted in any suitable manner. Laser diodes are polarized so a method of rotating the polarization by wave plates may be used with these light sources. For example, polarizer 714 shown in FIG. 7 may be a wave plate suitable for rotating the polarization of the light produced by the laser diodes.

In one embodiment, the illumination subsystem includes two or more light sources, and each of the two or more light sources is configured to provide light in only one of the discrete spectral bands. The two or more light sources may include any of the light sources described herein such as two or more broadband light sources, LEDs, or laser diodes. In addition, each of the two or more light sources may be configured to provide light in only one of the discrete spectral bands as described above. In other words, a first light source may provide light in only a first discrete spectral band, a second light source may provide light in only a second discrete spectral band different from the first, and so on.

Figure 9:
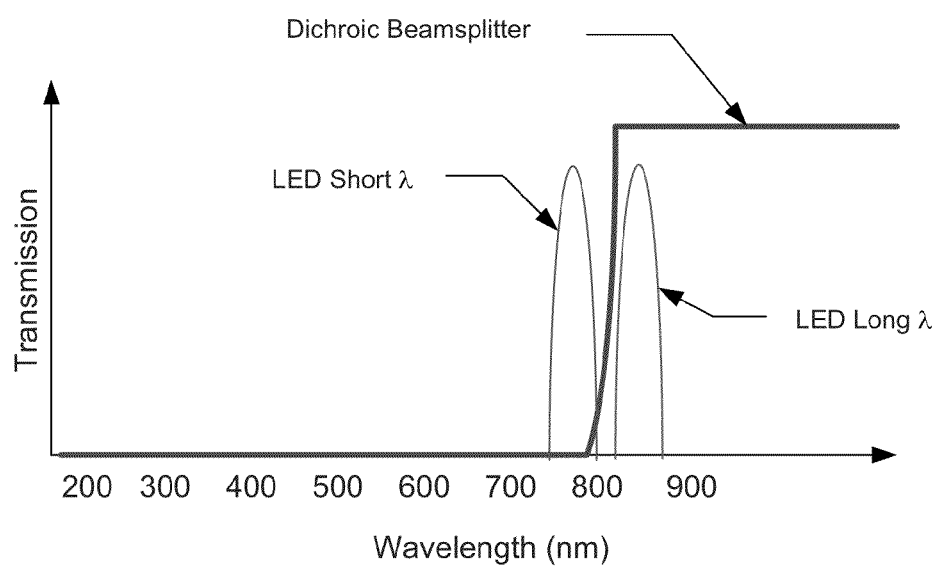
FIG. 9 is a plot illustrating the discrete spectral bands of light provided by two light emitting diodes (LEDs) that may be included in the system embodiments described herein and the transmission characteristics of a beam splitter that may be used to direct the light provided by both of the LEDs into a common illumination path.

In one such embodiment, the illumination subsystem includes one or more beam splitters configured to direct the light provided by each of the two or more light sources into a common illumination path. For example, the two or more light sources may include LEDs and, as shown in FIG. 9, one of the LEDs may provide light at shorter wavelengths (i.e., LED Short λ shown in FIG. 9), and another of the LEDs may provide light at longer wavelengths (i.e., LED Long λ shown in FIG. 9). As further shown in FIG. 9, the shorter wavelength LED may have a center wavelength at about 780 nm while the longer wavelength LED may have a center wavelength at about 820 nm. In addition, as shown in FIG. 9, the spectral bands of the two LEDs are discrete and separated in wavelength from one another.

For such light sources, the illumination subsystem may include a dichroic beam splitter that has the spectral characteristics shown in FIG. 9. For example, the dichroic beam splitter may have substantially zero transmission for wavelengths below about 800 nm and approximately 100% transmission for wavelengths above about 800 nm. In this manner, the dichroic beam splitter will reflect wavelengths below about 800 nm and transmit wavelengths above about 800 nm. As such, the beam splitter can direct the light provided by the two light sources shown in FIG. 9 into a common illumination path by reflecting the light provided by the shorter wavelength LED and transmitting the light provided by the longer wavelength LED.

Figure 10:
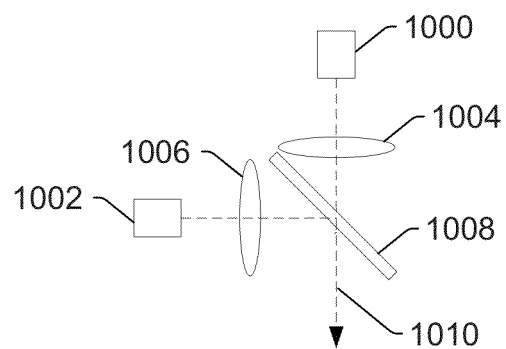
FIG. 10 is a schematic diagram illustrating a side view of one embodiment of two light sources that may be included in the system embodiments described herein and a beam splitter that may be used to direct the light provided by both of the light sources into a common illumination path.
Figure 11:
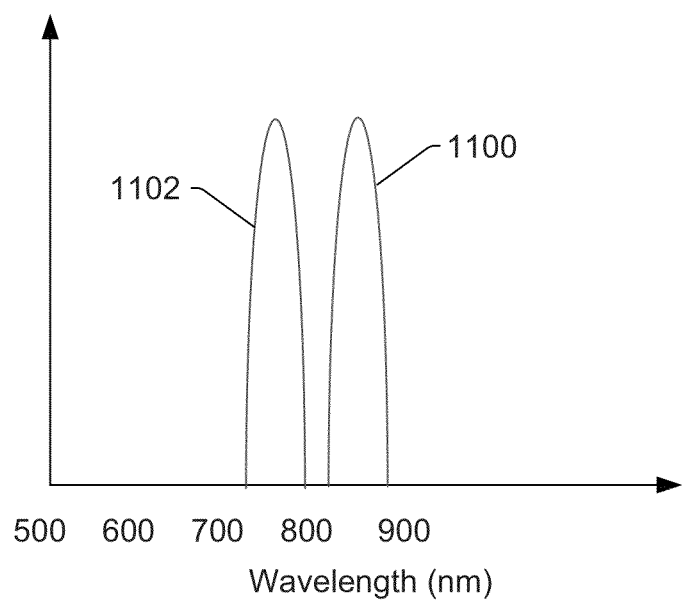
FIG. 11 is a plot illustrating the output spectrum of the LEDs shown in FIG. 9 after the light from the LEDs has been directed into a common illumination path as shown in FIG. 10.

As further shown in FIG. 10, the illumination subsystem may include LED 1000 configured to provide light at shorter wavelengths and LED 1002 configured to provide light at longer wavelengths. These LEDs may be further configured as described herein. In addition, as shown in FIG. 10, each of the LEDs may be coupled to a refractive optical element to collimate the light from the LED such as lens 1004 coupled to LED 1000 and lens 1006 coupled to LED 1002. The lenses may be, for example, relay lenses configured to direct the light from the light sources to beam splitter 1008. Beam splitter 1008 may be further configured as described above. For example, beam splitter 1008 may be a dichroic beam splitter that is configured to reflect the light from the longer wavelength LED and to transmit the light from the shorter wavelength LED such that the light from both LEDs is directed along common illumination path 1010. In this manner, the illumination subsystem may be configured to combine the output from two LEDs with a dichroic beam splitter that transmits the shorter wavelength LED source and reflects the longer wavelength LED source. Therefore, as shown in FIG. 11, the output spectrum from the LED pair after the dichroic beam splitter will be light in two discrete spectral bands 1100 and 1102 that are spaced apart in wavelength and may be centered, for example, at wavelengths of about 780 nm and about 820 nm. Any and all of the light sources described herein may, however, be selected for any suitable discrete spectral bands.

Figure 12:
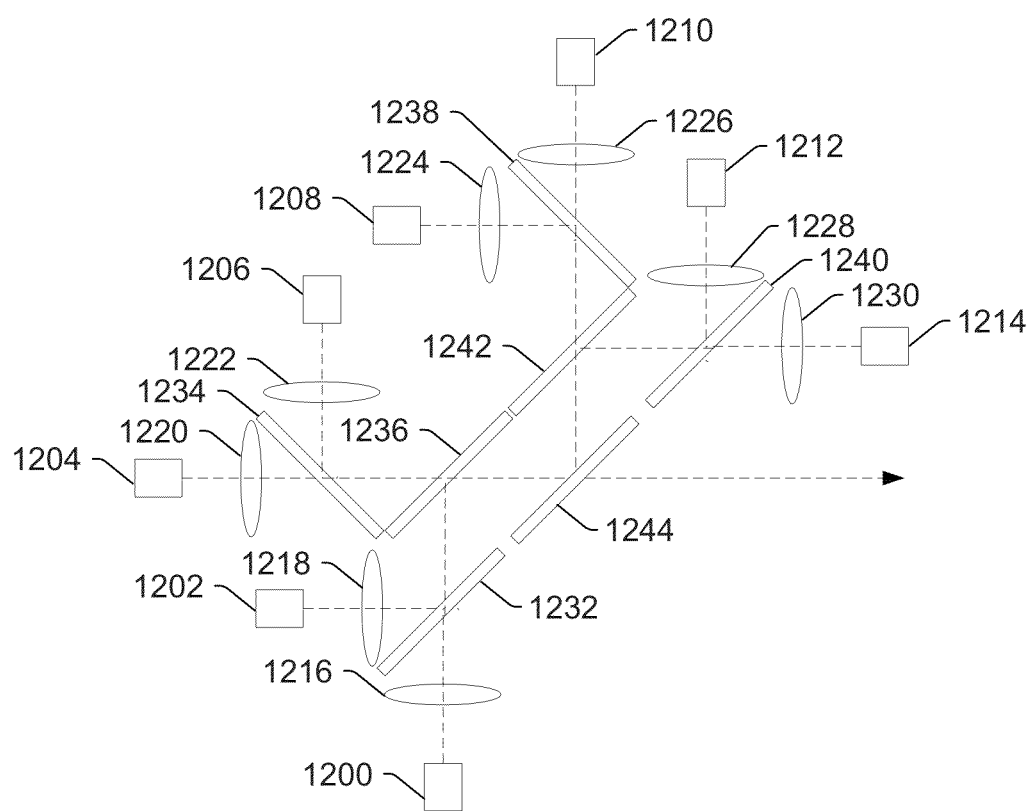
FIG. 12 is a schematic diagram illustrating a side view of one embodiment of 8 LEDs that may be included in the system embodiments described herein and beam splitters that may be used to direct the light provided by each of the LEDs into a common illumination path.

The optical configuration described above may, of course, be easily expanded to include more than two light sources that are combined by more than one beam splitter. For example, as shown in FIG. 12, the illumination subsystem may have an 8 LED combined spectral source layout. Multiple pairs of LED sources may be combined with multiple pairs of dichroic beam splitters. For example, the illumination subsystem may include LEDs 1200, 1202, 1204, 1206, 1208, 1210, 1212, and 1214, which may be configured as described above. Each of the LEDs may be coupled to at least one refractive optical element such as lenses 1216, 1218, 1220, 1222, 1224, 1226, 1228, and 1230, which may be configured as described above.

Beam splitter 1232 is configured to direct light from LEDs 1200 and 1202 along a common illumination path, and beam splitter 1234 is configured to direct light from LEDs 1204 and 1206 along a common illumination path. In this manner, the light exiting each of these beam splitters may include two discrete spectral bands. In addition, the light exiting both of these beam splitters may be directed along a common illumination path by beam splitter 1236. The light exiting this beam splitter will then have four discrete spectral bands.

In a similar manner, the light from LEDs 1208 and 1210 may be combined by beam splitter 1238, and the light from LEDs 1212 and 1214 may be combined by beam splitter 1240. The light exiting beam splitters 1238 and 1240 may then be combined by beam splitter 1242 into a common illumination path, and the light in that path will have four discrete spectral bands. The light from beam splitters 1236 and 1242 may then be further combined into another common illumination path by beam splitter 1244, and the light exiting this beam splitter will then have 8 discrete spectral bands. The beam splitters shown in FIG. 12 may include any suitable commercially available or specially designed dichroic beam splitters. In addition, each of the beam splitters shown in FIG. 12 may have different transmission/reflection characteristics from each other since each of the beam splitters will be reflecting or transmitting different wavelengths of light depending on its position within the optical configuration.

This light may then be directed to other components of the illumination subsystem described herein such as condenser 704 or polarizer 714 shown in FIG. 7. In other words, the light source shown in FIG. 7 may be replaced with the light source/beam splitter combinations shown in FIG. 10 or 12. In addition, the optical configuration shown in FIG. 12 can be made more compact than that shown in FIG. 12 by rotating some of the elements by 90 degrees. Furthermore, the configuration shown in FIG. 12 can be expanded to include more light sources or can be made smaller by including fewer light sources. Light from laser diodes or other sources can be combined in a similar manner to that shown in FIG. 12.

In another such embodiment, at least some of the two or more light sources are configured to emit different powers. For example, the two or more light sources may be selected for different powers or the powers of the light sources may be variable or controllable (e.g., by varying one or more parameters of the light sources themselves). In this manner, the discrete spectral bands of light directed to the wafer may have different powers.

Figure 13:
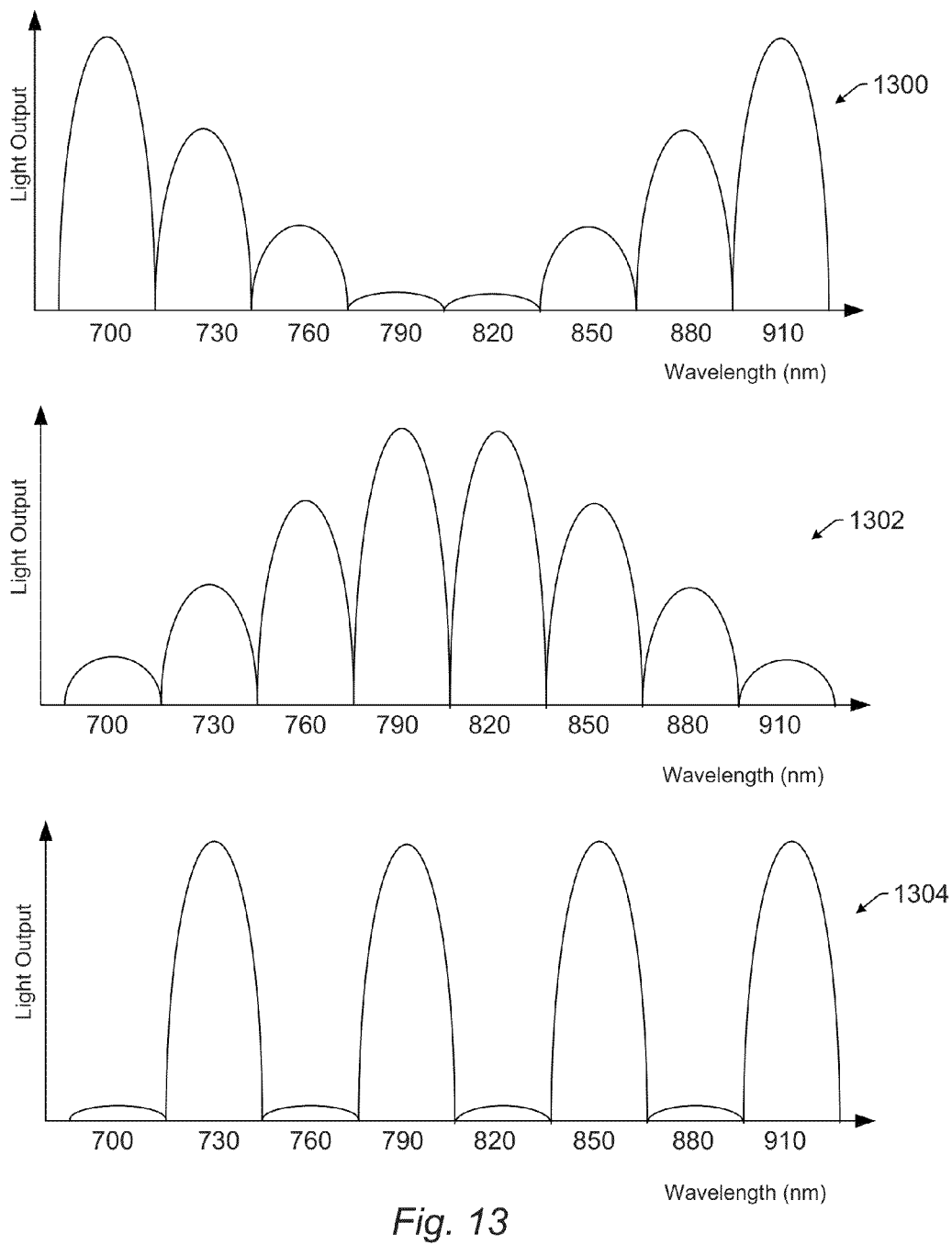
FIG. 13 includes plots illustrating different combined spectrums using LEDs having bandwidths spaced 30 nm apart with varying power on selected LEDs.

FIG. 13 shows examples of different combined spectrums using LEDs spaced 30 nm apart with varying power on selected LEDs to create various spectral outputs that are suited to the layer being inspected. For example, as shown in spectral output 1300, the power of the light in the middle discrete spectral bands may be the lowest of all of the spectral bands and may increase as the discrete spectral bands move away from the center overall wavelength. In contrast, as shown in spectral output 1302, the power of the light in the middle discrete spectral bands may be the highest of all the spectral bands and may decrease as the discrete spectral bands move away from the center overall wavelength. In another possibility shown in spectral output 1304, light in adjacent discrete spectral bands may have powers that alternate between the highest provided power and the lowest provided power. More specifically, the power of the spectral bandwidth centered at 700 nm may be low, while the power of the spectral bandwidth centered at 730 nm may be high, the power of the spectral bandwidth centered at 760 nm may be low, and so on.

As further shown in FIG. 13, some of the spectral bands have the same power while other spectral bands have different powers. However, each of the spectral bands may have a power that is different than the power of each other spectral band. Furthermore, the power of one or more of the spectral bands may be altered depending on the wafer (or layer on the wafer) being inspected. In this manner, the overall spectral shape provided by a combination of light sources in the system may be variable across wafers. In addition, as shown in FIG. 13, the illumination subsystem may be configured such that at least some light from all of the light sources included in the system is directed to the wafer. However, the power used for one or more of the spectral bands for any one wafer being inspected may be reduced to zero in some cases. In other words, inspection of a wafer may include illuminating the wafer with light from fewer than all of the light sources included in the system. In a similar manner, if the illumination subsystem includes a broadband light source as described further above, not all of the wavelengths of light produced by the broadband source may be directed to any given wafer being inspected. Instead, the wavelengths of the broadband source that are used for inspection may be selected by altering the spectral filter(s) positioned in the path of the light produced by the source.

In a further such embodiment, the illumination subsystem includes one or more elements configured to alter the output power of the light provided by at least one of the two or more light sources such that the light in at least two of the discrete spectral bands directed to the wafer has different light output powers. For example, as described above, the illumination subsystem may alter one or more parameters of the light sources themselves to alter the output power of the light sources. In one such example, the one or more elements may include individual controllers (not shown), one coupled to each light source, that can separately and independently alter the output power of the light sources. In another example, the one or more elements may include optical elements that are or can be positioned in the path of the light from each of the light sources independently. For example, the refractive optical elements shown in FIG. 12 (e.g., lenses 1216, 1218, etc.) may be replaced with spectral filters such as multiple neutral density filters that can be independently positioned by the system in the path of each of the light sources. The refractive optical elements may also be replaced with optical elements such as liquid crystal devices that can change the power of the light transmitted to other optical elements of the illumination subsystem without being moved into and out of the path of the light.

In summary, therefore, the system embodiments described herein provide wafer inspection systems configured to operate at NIR wavelengths using optionally polarized light with multiple spectral bands, each having a bandpass less than 100 nm, for the inspection of 3D wafer structures. Such embodiments have a number of advantages over currently available systems. For example, as described further herein, the embodiments can be used to distinguish defect depth by wavelength penetration, where longer wavelengths "see" defects lower in the structure (either a trench etch in an opaque material or penetrating silicon, amorphous, and/or polysilicon materials). Since the wavelengths used by the embodiments described herein can penetrate into such materials, the defects detected by the embodiments may include so called "buried" defects, or defects that are located completely within a material.

Any of the defect information generated by the embodiments described herein may be used to generate a map of the defects across the wafer (a "wafer" or "defect" map). Different wafer maps can be generated for defects detected at different depths in the wafer. In this manner, the different wafer maps can be used to identify different signatures in the defects that are present at different depths in the wafer. The signature can change quite dramatically with wavelength over the NIR range as the embodiments view further into the wafer finding different populations of defects. For example, unique signatures can be found in different portions of the wafer (near the center versus near the edge) for different discrete spectral bands. Such information about the defects versus depth in the wafer can provide highly useful information about the process(es) used to form structures on the wafer.

In addition, the relatively small bandpass allows higher signals to pick a maximum signal wavelength, since if the signals oscillate rapidly with wavelength, a larger waveband will average the oscillations with a lower signal. Furthermore, the embodiments may be used to identify the depth of a defect and/or its type by comparing an observed signal vs. wavelength and/or aperture to a set of simulated signal vs. wavelength and/or aperture and using the best match to determine the defect depth and/or type.

Each of the system embodiments described above may be configured to perform any step(s) of any method(s) described herein. In addition, each of the system embodiments described herein may be configured according to any other embodiments or systems described herein.

Another embodiment relates to a method for detecting defects in one or more structures formed on a wafer. The method includes directing light in discrete spectral bands to the one or more structures formed on the wafer, which may be performed according to any embodiments described herein. At least some of the discrete spectral bands are in the NIR wavelength range. In addition, each of the discrete spectral bands has a bandpass that is less than 100 nm. The discrete spectral bands may be further configured according to any of the embodiments described herein. The one or more structures may include any of the one or more structures described herein. The method also includes generating output responsive to light in the discrete spectral bands reflected from the one or more structures, which may be performed according to any of the embodiments described herein. In addition, the method includes detecting defects in the one or more structures on the wafer using the output, which may be performed according to any of the embodiments described herein.

Each of the embodiments of the method described above may include any other step(s) of any other method(s) described herein. In addition, each of the embodiments of the method described above may be performed by any of the systems described herein.

Figure 14:
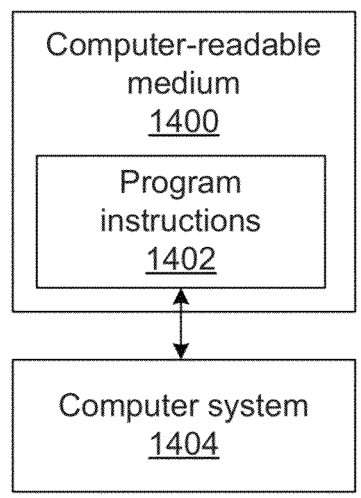
FIG. 14 is a block diagram illustrating one embodiment of a non-transitory computer-readable medium.

Another embodiment relates to a non-transitory computer-readable medium containing program instructions stored therein for causing a computer system to perform a computer-implemented method for detecting defects in one or more structures formed on a wafer. One embodiment of such a computer-readable medium is shown in FIG. 14. In particular, computer-readable medium 1400 contains program instructions 1402 stored therein for causing computer system 1404 to perform a computer-implemented method for detecting defects in one or more structures formed on a wafer.

The computer-implemented method includes any step(s) described above with respect to the computer subsystem of the system. For example, the computer-implemented method may include detecting defects in the one or more structures using output that is responsive to light in the discrete spectral bands reflected from the one or more structures. The computer-implemented method may also include any other step(s) of any other method(s) described herein. In addition, the computer-readable medium may be further configured as described herein.

Program instructions 1402 implementing methods such as those described herein may be stored on computer-readable medium 1400. The computer-readable medium may be a non-transitory computer-readable storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

Computer system 1404 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

Further modifications and alternative embodiments of various aspects of the invention will be apparent to those skilled in the art in view of this description. For example, multi-spectral defect inspection for 3D wafers is provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to detect defects in one or more structures formed on a wafer, comprising:

an illumination subsystem configured to direct light in discrete spectral bands to the one or more structures formed on the wafer, wherein at least some of the discrete spectral bands are in a near infrared wavelength range, wherein each of the discrete spectral bands has a bandpass that is less than 100 nm, wherein the illumination subsystem comprises first and second apertures that are different from each other, and wherein the illumination subsystem is further configured to scan the light in the discrete spectral bands across the wafer using the first aperture and then the second aperture;

a detection subsystem configured to generate output responsive to light in the discrete spectral bands reflected from the one or more structures; and a computer subsystem configured to detect defects in the one or more structures on the wafer using the output, wherein the computer subsystem is further configured to detect the defects in the one or more structures on the wafer using the output generated by scanning performed with the first and second apertures.

2. The system of claim 1, wherein the one or more structures are formed through a stack of two or more layers of material, and wherein the stack has a thickness greater than at least 1 um.

3. The system of claim 1, wherein the one or more structures comprise one or more opaque metallic structures formed through a stack of two or more layers of material.

4. The system of claim 1, wherein the one or more structures are formed through a stack of two or more layers of material, and wherein at least some of the two or more layers comprise polysilicon.

5. The system of claim 1, wherein the one or more structures are formed through a stack of two or more layers of material, and wherein at least some of the two or more layers comprise an opaque conductor.

6. The system of claim 1, wherein each of the discrete spectral bands is separated by a wavelength of at least 1 nm.

7. The system of claim 1, wherein the discrete spectral bands are in a wavelength. range from 500 nm to 950 nm.

8. The system of claim 1, wherein the light directed by the illumination subsystem to the one or more structures penetrates to different depths in the one or more structures depending on the discrete spectral bands of the light.

9. The system of claim 1, wherein the illumination subsystem further comprises a broadband light source configured to generate at least two of the discrete spectral bands of light.

10. The system of claim 9, wherein the illumination subsystem further comprises two or more spectral filters configured to be positioned in a path of the light generated by the broadband light source, wherein different spectral filters correspond to different discrete spectral bands, and wherein the illumination subsystem is further configured to sequentially position the spectral titters in the path such that the light in the discrete spectral bands is sequentially directed to the wafer.

11. The system of claim 1, wherein the illumination subsystem further comprises light emitting diodes, wherein each of the light emitting diodes is configured to provide the light in only one of the discrete spectral bands, and wherein each of the light emitting diodes has a bandwidth that is spaced from bandwidths of other light emitting diodes in the illumination subsystem by at least 20 nm.

12. The system of claim 1, wherein the illumination subsystem further comprises laser diodes, wherein each of the laser diodes is configured to provide the light in only one of the discrete spectral bands, and wherein each of the laser diodes has a bandwidth that is spaced from bandwidths of other laser diodes in the illumination subsystem by at least 20 nm.

13. The system of claim 1, wherein the illumination subsystem further comprises two or more light sources, and wherein each of the two or more light sources is configured to provide light in only one of the discrete spectral bands.

14. The system of claim 13, wherein the illumination subsystem further comprises one or more beam splitters configured to direct the light provided by each of the two or more light sources into a common illumination path.

15. The system of claim 13, wherein at least some of the two or more light sources are configured to emit different powers.

16. The system of claim 13, wherein the illumination subsystem further comprises one or more elements configured to alter the output power of the light provided by at least one of the two or more light sources such that the light in at least two of the discrete spectral bands directed to the wafer has different light output powers.

17. The system of claim 1, wherein the One or more structures are formed through a stack of two or more layers of material, and wherein the illumination subsystem further comprises a polarizing component configured to alter a polarization of the light directed by the illumination subsystem to the one or more structures such that the polarization of the light is substantially perpendicular to the one or more structures.

18. The system of claim 1, wherein the one or more structures comprise one or more trenches formed through a stack of two or more layers of material, and wherein the illumination subsystem further comprises a polarizing component configured to alter a polarization of the light directed by the illumination subsystem to the one or more trenches such that the polarization of the light is substantially perpendicular to the one or more trenches.

19. The system of claim 18, wherein at least one of the two or more layers of material in the stack comprises tungsten.

20. The system of claim 1, wherein the one or more structures are formed through a stack of two or more layers of material, and wherein the computer subsystem is further configured to determine a location of the defects within the stack.

21. The system of claim 1, wherein the one or more structures are formed through a stack of two or more layers of material, and wherein the computer subsystem is further configured to determine a type of the defects.

22. A method for detecting defects in one or more structures formed on a wafer, comprising:
- directing light in discrete spectral bands to the one or more structures formed on the wafer, wherein at least some of the discrete spectral bands are in a near infrared wavelength range, wherein each of the discrete spectral bands has a bandpass that is less than 100 nm, wherein said directing comprises scanning the light in the discrete spectral bands across the wafer using a first aperture and then a second aperture, and wherein the first and second apertures are different from each other;
- generating output responsive to light in the discrete spectral bands reflected from the one or more structures; and
- detecting defects in the one or more structures on the wafer using the output generated by the scanning performed with the first and second apertures.

* * * * *